US010849794B2

(12) United States Patent
Ueda

(10) Patent No.: US 10,849,794 B2
(45) Date of Patent: Dec. 1, 2020

(54) WOUND DRESSING

(75) Inventor: Atsushi Ueda, Tokyo (JP)

(73) Assignee: ALCARE CO., LTD., Tokyo (JP)

(*) Notice: Subject to any disclaimer, the term of this patent is extended or adjusted under 35 U.S.C. 154(b) by 169 days.

(21) Appl. No.: 13/816,969

(22) PCT Filed: Mar. 1, 2012

(86) PCT No.: PCT/JP2012/055162
§ 371 (c)(1),
(2), (4) Date: Feb. 14, 2013

(87) PCT Pub. No.: WO2013/128606
PCT Pub. Date: Sep. 6, 2013

(65) Prior Publication Data
US 2014/0024989 A1 Jan. 23, 2014

(51) Int. Cl.
A61F 13/00 (2006.01)
A61F 13/02 (2006.01)

(52) U.S. Cl.
CPC ........ A61F 13/0253 (2013.01); A61F 13/025 (2013.01); A61F 2013/00519 (2013.01);
(Continued)

(58) Field of Classification Search
CPC ................ A61F 13/0246; A61F 13/025; A61F 13/0253; A61F 2013/00519; A61F 2013/00702; A61F 2013/00697; A61F 2013/00719; A61F 2013/00782; A61F 2013/00761; A61F 2013/00774; A61F 2013/00778; A61F 2013/00655
(Continued)

(56) References Cited

U.S. PATENT DOCUMENTS 4,921,704 A * 5/1990 Fabo ................. A61F 13/00021
424/446
4,984,570 A * 1/1991 Langen .................. D04B 21/14
602/44
(Continued)

FOREIGN PATENT DOCUMENTS

JP 2005-154394 A 6/2005
JP 2008-29814 A 2/2008
(Continued)

OTHER PUBLICATIONS

PCT/ISA/210—International Search Report dated May 15, 2012, issued in PCT/JP2012/055162.
(Continued)

Primary Examiner — Victoria J Hicks
(74) Attorney, Agent, or Firm — Birch, Stewart, Kolasch & Birch, LLP

(57) ABSTRACT

A wound dressing having a perforated material including through-holes. The perforated material having a first and second face. A low adhesive resin coating at least the first face of the perforated material without closing the through holes. The perforated material is a knitted fabric or a woven fabric formed of a multifilament. The perforated material has an average opening area of the through-holes of 0.02 to 1.2 $mm^2$ and an average number of through-holes of 40 to 220 $cm^{-2}$.

8 Claims, 3 Drawing Sheets
(1 of 3 Drawing Sheet(s) Filed in Color)

(52) U.S. Cl.
CPC .............. *A61F 2013/00702* (2013.01); *A61F 2013/00719* (2013.01); *A61F 2013/00723* (2013.01); *A61F 2013/00782* (2013.01)

(58) Field of Classification Search
USPC ..... 602/44, 43, 54, 42, 41, 47, 55; 424/443; 442/123
See application file for complete search history.

(56) References Cited

U.S. PATENT DOCUMENTS

| | | | |
|---|---|---|---|
| 6,685,682 B1 * | 2/2004 | Heinecke | A61F 13/023 602/41 |
| 2006/0154546 A1 | 7/2006 | Murphy et al. | |
| 2008/0095979 A1 | 4/2008 | Hatanaka et al. | |
| 2010/0069858 A1 | 3/2010 | Olson | |
| 2011/0160686 A1 | 6/2011 | Ueda et al. | |
| 2011/0193257 A1 | 8/2011 | Matt et al. | |
| 2014/0364788 A1 | 12/2014 | Lecomte et al. | |

FOREIGN PATENT DOCUMENTS

| | | |
|---|---|---|
| JP | 2008-142264 A | 6/2008 |
| JP | 2009-95476 A | 5/2009 |
| JP | 2009095476 A * | 5/2009 |
| JP | 2011-530344 A | 12/2011 |
| JP | 2012-502745 A | 2/2012 |
| WO | WO 2010/017437 A1 | 2/2010 |
| WO | WO 2010/033574 A1 | 3/2010 |
| WO | WO 2013/093298 A1 | 6/2013 |

OTHER PUBLICATIONS

PCT/ISA/220—dated May 15, 2012, issued in PCT/JP2012/055162.
PCT/ISA/237—dated May 15, 2012, issued in PCT/JP2012/055162.
"Fiber Dictionary," Ed. Xing Shengyuan, Beijing, Chemical Industry Press, 2007, 10.
Second Notification of Reasons for Refusal dated Apr. 1, 2016, in Chinese Patent Application No. 201280003313.1, with English translation.
Author Unknown, "Spinning goods inspection," Chinese Goods Publisher in Beijing, 2006, p. 14 (6 pages total).
Partial English translation of the Chinese Office Action for corresponding Chinese Application No. 201810171067.X, dated May 28, 2020.

* cited by examiner

[FIG. 1]
(A)
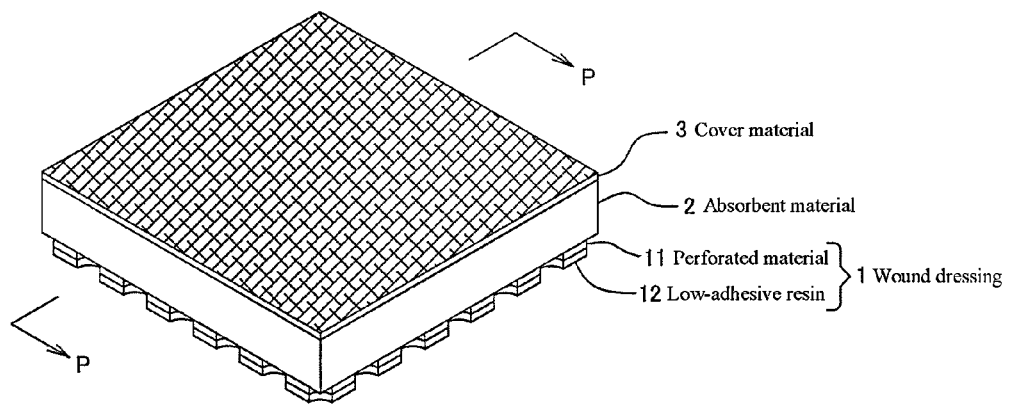
(B)
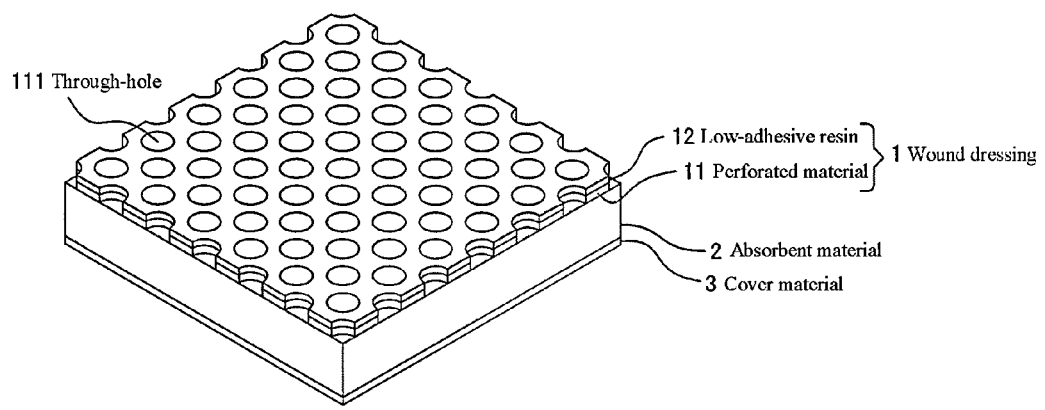
(C)
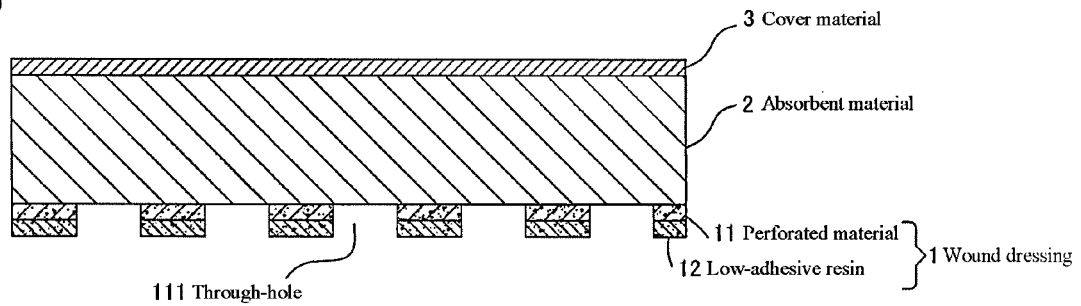

[FIG. 2]
(A)
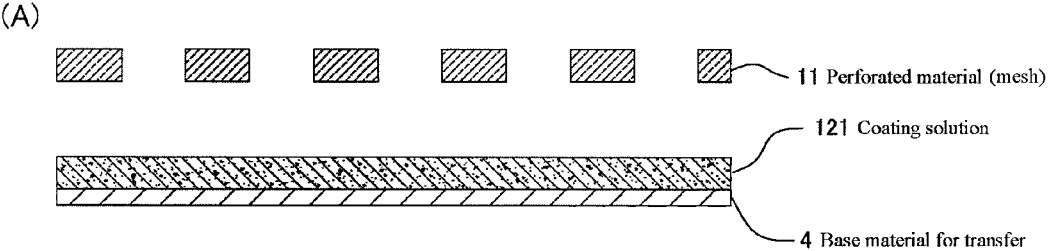
(B)
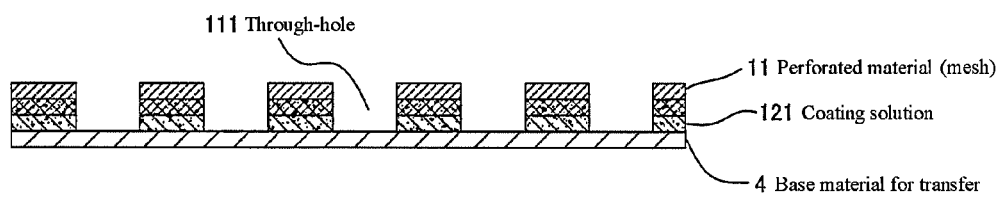
(C)
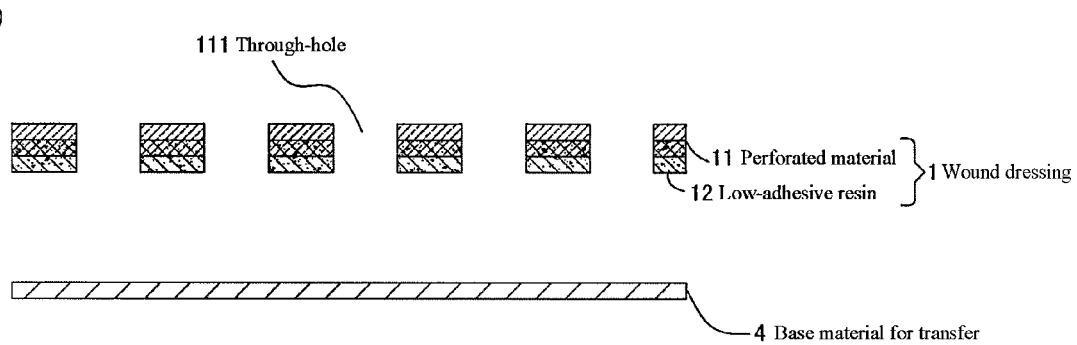
(D)
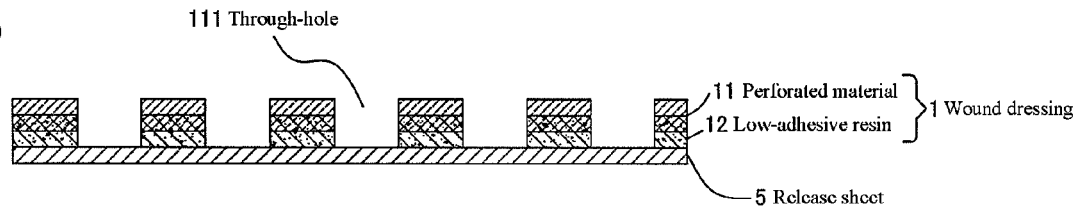

[FIG. 3]
(A) Example 1
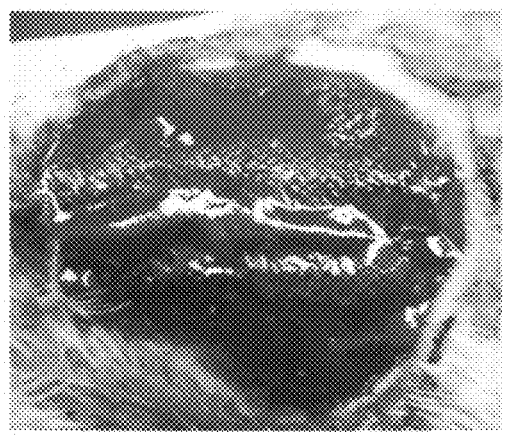
(B) Example 2
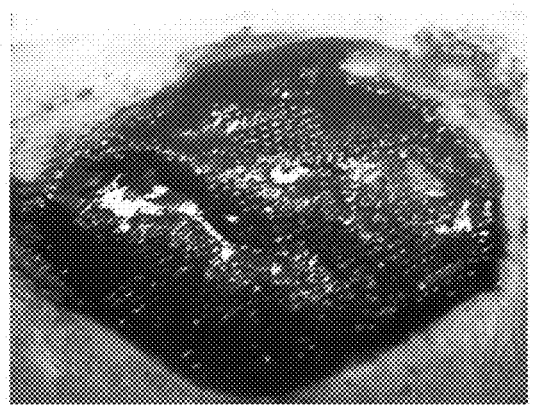
(C) Comparative Example 1
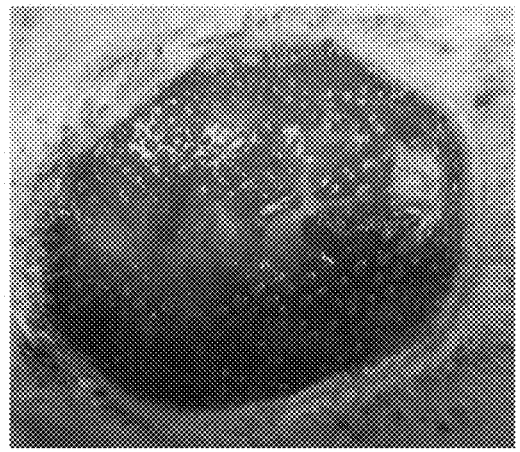
(D) Comparative Example 3
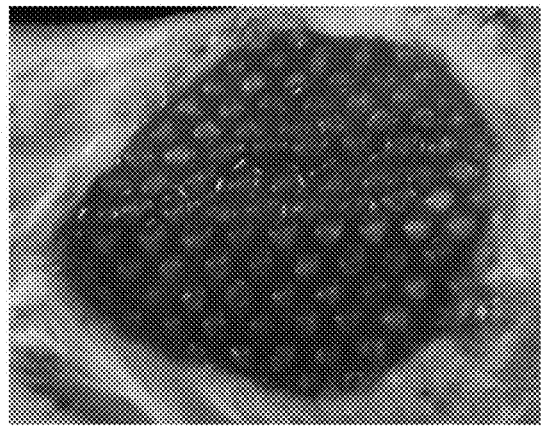

WOUND DRESSING

TECHNICAL FIELD

The present invention relates to a wound dressing. More specifically, the present invention relates to a wound dressing including a perforated material coated with a low-adhesive resin.

BACKGROUND ART

In order to protect a wound area such as a skin injury area due to burns, pressure ulcers, and other injuries and a skin grafted area, wound dressings in which an adhesive layer is formed using a silicone resin have been conventionally used. By using a low adhesive silicone resin as the adhesive layer, a wound dressing that is unlikely to adhere to a wound area can be obtained.

For example, Patent Document 1 discloses a wound dressing in which a silicon gel seals all components of an elastic net-like reinforcement except through-holes of the net-like reinforcement. When the wound dressing of Patent Document 1 is used in combination with an absorbent material in order to treat exudate, the absorbent material is exposed out through the part of the through-holes of the wound dressing. On this account, the wound dressing involves a risk of easy adhering to the neogenetic tissue of a wound area in the part of the through-holes.

Patent Document 2 teaches a wound dressing in which one face of an air-impervious and body fluid-impervious perforated layer material (carrier material) is coated with a silicone gel and an absorbent material is further included. As with the wound dressing of Patent Document 1, in the wound dressing of Patent Document 2, the applied absorbent material is kept exposed out through the part of the through-holes. Therefore, Patent Document 2 still cannot solve the problem of easy adhering of the wound dressing to neogenetic tissues.

Patent Document 3 discloses a wound dressing that includes a perforated material (mesh) having through-holes and an absorbent material disposed on one face of the perforated material and in which the other face of the perforated material is coated with a silicone resin and a part of the absorbent material corresponding to the through-holes is also coated with the silicone resin. In the wound dressing of Patent Document 3, both the perforated material to be in contact with a wound and the absorbent material are coated with the silicone resin. Thus, even when a neogenetic granulation tissue invades the perforated material through the through-holes, the wound dressing can be prevented from firmly adhering to the wound surface, and therefore the wound dressing can be removed and exchanged without damaging the fragile neogenetic epidermal tissue.

CITATION LIST

Patent Documents

[Patent Document 1] Japanese Patent No. 2525215
[Patent Document 2] Japanese Patent No. 3677283
[Patent Document 3] International Patent Application Publication No. WO 2010/122665

SUMMARY OF INVENTION

Technical Problem

In the wound healing process, neogenetic granulation tissues gradually grow upward. Hence, when a perforated material and an absorbent material are used to treat a wound, it should be considered that the granulation tissues invade the perforated material through through-holes and firmly adhere to the absorbent material. As the method of inhibiting the adhesion of the absorbent material to the granulation tissues, in addition to the technique disclosed in Patent Document 3, there may be a method by reducing the pore size of through-holes to inhibit the invasion of granulation tissues. However, when the pore size of the through-holes of the perforated material is reduced, it is difficult to apply a low-adhesive resin onto the perforated material without closing the through-holes of the perforated material. Hence, such a wound dressing may prevent exudate from passing through the perforated material.

Therefore, the present invention has an object to provide a wound dressing that includes a perforated material having through-holes and has adhesion prevention properties to wounds. The present invention also has an object to provide a wound dressing that includes a perforated material having through-holes with a small pore size and in which the perforated material is coated with a low-adhesive resin without closing the through-holes of the perforated material.

Solution to Problem

For solving the above-mentioned problems, the invention provides a wound dressing that includes a first layer of perforated material including through-holes, and a second layer of low-adhesive resin coating at least one face of the perforated material without closing the through-holes, in which the perforated material is a knitted fabric or a woven fabric formed of a multifilament, and the perforated material has an average opening area of the through-holes of 0.02 to 1.2 mm$^2$ and an average number of through-holes of 40 to 220 holes/cm$^2$. None of the perforated material is encapsulated by the low-adhesive resin. The wound dressing is built in layers. By designing the opening area of the through-hole and the number of through-holes in the perforated material within the particular numerical ranges, such a wound dressing can be prevented from adhering to granulation tissues that invade the through-holes.

In the wound dressing, it is preferable that the multifilament include 15 to 100 filaments. By designing the number of filaments in the multifilament within the particular numerical range, clogging of the through-holes by the low-adhesive resin can be suppressed when the low-adhesive resin is applied to the perforated material.

In the wound dressing, it is preferable that one face alone of the perforated material be coated with the low-adhesive resin. It is preferable that the low-adhesive resin be a silicone resin.

Advantageous Effects of Invention

The present invention provides a wound dressing that includes a perforated material including through-holes, in which the perforated material can be coated with a low-adhesive resin without closing the through-holes, and that has excellent adhesion prevention properties to wounds.

BRIEF DESCRIPTION OF DRAWINGS

The patent or application file contains at least one color drawing. Copies of this patent or patent application publication with color drawing will be provided by the USPTO upon request and payment of the necessary fee.

FIG. 1 are drawings showing the structure of a wound dressing of the present invention.

FIG. 2 are drawings showing each process of a method for producing the wound dressing of the present invention.

FIG. 3 are photographs in place of drawings showing evaluation results of cosmetic results on wound surfaces treated with wound dressings produced in examples.

DESCRIPTION OF EMBODIMENTS

Preferred embodiments for carrying out the present invention will now be described. The embodiments described below are examples of typical embodiments of the present invention and the embodiments are not intended to limit the scope of the invention.
1. Wound Dressing
(1) Perforated Material FIG. 1 are drawings showing the structure of a wound dressing of the present invention. FIG. 1(A) is a top perspective view, FIG. 1(B) is a bottom perspective view, and FIG. 1(C) is a sectional view taken along the line P-P in FIG. 1(A).

A wound dressing 1 includes a sheet-shaped perforated material 11 (hereinafter also referred to as "mesh 11") having through-holes 111 and a gel-like low-adhesive resin 12 with which one face of the mesh 11 is coated. Both faces of the mesh 11 may be coated with the low-adhesive resin 12. The wound dressing 1 has a release sheet (not shown in drawings) laminated on the low-adhesive resin 12.

The wound dressing 1 is preferably used in combination with an absorbent material 2 and a cover material 3. Specifically, after removing the release sheet, the wound dressing 1 is attached so that the low-adhesive resin 12 is in contact with a wound area such as a skin injury area and a skin grafted area. The absorbent material 2 is disposed on the wound dressing 1 in order to absorb exudate (containing blood) bleeding from the wound area through the through-holes 111 of the wound dressing 1. The absorbent material 2 to be used may be a conventionally known material. Usable examples of the absorbent material 2 include a fibrous material such as a nonwoven fabric, a knitted fabric, and a woven fabric, a foam material, an absorbing resin material, and a water-absorbing powdery material.

The cover material 3 covers the top face of the absorbent material 2 and works, for example, for protecting the absorbent material 2 from contamination and for preventing a contaminant such as exudate from removing from the absorbent material 2. One side of the cover material 3 is coated with an adhesive, and the cover material 3 may be attached to the absorbent material 2 so that the cover material 3 is extended beyond the outer edge of the absorbent material 2 (not shown in drawings). The cover material 3 extended beyond the outer edge of the absorbent material 2 enables easy fixing of the wound dressing 1 and the absorbent material 2 to a wound area. The cover material 3 to be used may be a conventionally known material. Usable examples of the cover material 3 include a fibrous sheet such as a nonwoven fabric, a knitted fabric, a woven fabric, and a net, a synthetic resin film, and a foam. The use of a liquid-impervious but water vapor-pervious plastic film as the cover material 3 enables to prevent exudate from leaking from the outer edge of the absorbent material even when the exudate is excess and enables to maintain a wound in an appropriate moist environment, thereby promoting wound healing.

The mesh 11 is a knitted fabric or a woven fabric formed of a multifilament. The mesh 11 has a sheet shape with a top face and a bottom face. A wound dressing 1 using a fiber material as the mesh 11 to be a base material can obtain higher following performance to any unevenness comparing with the case in which a synthetic resin film material is used as the base material. The higher following performance to any concave-convex increases the adhesiveness to a wound area. Therefore, the wound dressing 1 is not unexpectedly removed or displaced from a wound area even when the low-adhesive resin 12 has a low adhesive power. In addition, such a low-adhesive resin 12 having a low adhesive power can reduce the damage to a wound area when the wound dressing 1 is removed.

The mesh 11 may adopt a mesh including through-holes 111 formed by knitted loops of a knitted fabric, a mesh including through-holes 111 formed by the balance of a knitted texture (including the thickness and the density of yarn), or a mesh including through-holes 111 as voids formed between the warp and the weft of a woven fabric. In the case, the knitted texture or the woven texture is not particularly limited as long as such a texture includes a predetermined number of through-holes 111 having a predetermined size as described next. The knitted fabric or the woven fabric may be a fabric having through-holes 111 that are physically formed by penetration in a post process. In the case, the knit texture or the woven texture is not limited specifically.

The mesh 11 is preferably a knitted fabric including through-holes 111 formed by knitted loops of the knitted fabric or a knitted fabric including through-holes 111 formed by the balance of a knitted texture. This is because these knitted fabrics are especially excellent in following performance to any concave-convex.

The multifilament constituting a knitted fabric or a woven fabric of the mesh 11 preferably includes 15 to 100 filaments and more preferably includes 20 to 80 filaments. By designing the number of filaments included in the multifilament within the numerical range, the through-holes 111 can be prevented from being closed by the low-adhesive resin 12 when the mesh 11 is coated with the low-adhesive resin 12 (described later in detail). When using a multifilament in which the number of filaments is within the range, each filament preferably has a diameter of 1 to 100 μm and more preferably 5 to 50 μm. By designing the diameter of the filament within the numerical range, the obtained multifilament enables easy formation of through-holes in the mesh 11 having a desired opening area and a desired perforated rate.

The type of the multifilament and the type of filaments constituting the multifilament are not particularly limited. Usable examples include a polyester fiber, an acrylic fiber, a polyamide fiber, a polyurethane fiber, a cellulose fiber (cotton, rayon, polynosic, and lyocell), a polyolefin fiber, a polyvinyl chloride fiber, a polyvinylidene chloride fiber, a glass fiber, and a carbon fiber.

The mesh 11 preferably has a thickness of 50 to 1,000 μm and more preferably 100 to 500 μm. A mesh having a thickness of less than 50 μm is limp, has poor handleability, and reduces the amount of low-adhesive resin that can be held by the mesh, and therefore such a mesh may cause clogging of the through-holes. In contrast, a mesh having a thickness of more than 500 μm raises problems in following performance and adhesion to a wound surface.

(2) Through-Hole

The through-hole 111 preferably provides an average opening area of 0.02 to 1.2 $mm^2$ and more preferably 0.08 to 0.8 $mm^2$. When the opening area of the through-hole 111 is more than 1.2 $mm^2$, granulation tissues regenerated from a wound area invade through the through-holes 111 and are likely to adhere to the absorbent material 2. When the average opening area of the through-holes 111 is more than 1.2 mm$^2$, the regenerated granulation tissues invade the through-holes 111 and the granulation tissues form an uneven wound face corresponding to the shape of a hole wall face of the through-holes (see FIGS. 3(C) and 3(D) shown later). A wound surface does not become flat but becomes uneven in a healing process and this may require time for finely healing the wound. When the average opening area of the through-holes 111 is less than 0.02 mm$^2$, the exudate from a wound area is difficult to move through the through-holes 111 to the absorbent material 2 and this reduces the function of treating exudate. A through-hole 111 providing an average opening area of less than 0.02 mm$^2$ is likely to cause clogging of the through-holes 111 when the mesh 11 is coated with the low-adhesive resin 12 (described later in detail). The opening area of the through-hole 111 is technically equivalent to the pore size of the through-hole 111.

The average number of the through-holes 111 is preferably 40 to 220 cm$^{-2}$ and more preferably 80 to 200 cm$^{-2}$. The mesh 11 preferably has a perforated rate of 25 to 90% and more preferably 30 to 85%, where the perforated rate is calculated from the average opening area and the average number of the through-holes 111. By designing the average through-hole number and the perforated rate within the preferred numerical ranges, combined with the preferred range of the average opening area of the through-holes 111, the exudate treatment performance through the through-holes 111 is increased, non-adhesion properties is increased because granulation invasion is prevented, and the wound dressing 1 obtains, for example, excellent handleability.

The arrangement of the through-holes 111 is not particularly limited. The through-holes may be scattered in a regular manner or in a random manner or may be arranged to form a certain pattern such as a grid pattern, a wavelike pattern, a concentric pattern, and a spiral pattern. The through-holes 111 are preferably arranged at equal intervals so as to ensure uniform exudate penetration over the whole mesh 11.

(3) Low-Adhesive Resin

The low-adhesive resin 12 may be any resin as long as the resin has adhesiveness to such a degree that the resin does not cause much irritate or damage to a skin and a wound when the wound dressing 1 of the present invention is applied to the wound area and is removed from the area. The low-adhesive resin 12 includes a natural or synthetic polymer, a mixture of a plurality of such polymers, or a mixture of such a polymer and other substances. The low-adhesive resin used in the present invention may be either hydrophobic or hydrophilic and may be combined with an appropriate liquid substance to be used in the form of an organogel or a hydrogel. The low-adhesive resin may also be blended with a hydrophilic polymer compound to be used in the form of a so-called hydrocolloid. In particular, the low-adhesive resin is preferably a resin containing a hydrophobic resin as a main component and is particularly preferably used in the form of a hydrophobic gel. As the hydrophobic resin, a resin that forms a layer having a surface providing a contact angle of 65° or more with water may be selected. Such a resin can be exemplified by one or more resins selected from the group consisting of a silicone resin, an acrylic resin, a methacryl resin, a polyvinyl chloride resin, a polyvinylidene chloride resin, a fluorine resin, an olefinic resin, a polyester resin, a styrene resin, an urethane resin, a polyamide resin, and mixtures of them. Among these low-adhesive resins, a silicone resin is particularly preferred because it is easy in handling and is unlikely to adhere to a wound area. The silicone resin is especially preferably cured into a gel form by, for example, cross-linking. The curing method of the silicone resin is not particularly limited and the silicone resin can be easily cross-linked by, for example, heating.

The silicone resin may be an addition reaction-type silicone resin, a peroxide reaction-type silicone resin, or a condensation reaction-type silicone resin, but is preferably an addition reaction-type silicone resin. Silicone resins may be used singly or in combination of two or more of them.

The addition reaction-type silicone resin is obtained by addition reaction (hydrosilylation reaction) of an organo polysiloxane having an alkenyl group bonded to a silicon atom (alkenyl group-containing organo polysiloxane) and an organo polysiloxane having a hydrosilyl group (Si—H) (hydrogen-organo polysiloxane) using a platinum compound catalyst such as chloroplatinic acid. The cross-linking density of an addition reaction-type silicone resin can be controlled by changing the amount of an organo hydrogen polysiloxane to be used for the synthesis or the amount of the hydrosilyl group (Si—H) in an organo hydrogen polysiloxane molecule. This enables easy control of the hardness or the adhesive power of a silicone resin. The addition reaction-type silicone resin is preferably an addition reaction product of a vinyl group-substituted polydimethylsiloxane and an organo hydrogen polysiloxane.

The silicone resin may suitably contain a medicinal agent, a water-absorbing polymer compound, and other controlling agents such as a pH controlling agent as long as an object of the present invention is not impaired.

Examples of the medicinal agent include a substance for regulating the physiological function of skin for the purpose of moisturization, antiaging, whitening, and the like, a substance for promoting wound healing, and a substance having antimicrobial activity. Specific example of the medicinal agent include sphingolipids, urea, glycolic acid, amino acids and derivatives of them (such as arginine, cysteine, glycine, lysine, proline, and serine), protein hydrolysates (such as collagen, elastin, and keratin), mucopolysaccharides and derivatives of them (such as hyaluronic acid, chondroitin sulfate, and heparin), vitamin B groups (such as thiamine, riboflavin, nicotinic acid, pyridoxine, pyridoxal, pyridoxamine, biotin, folic acid, and cyanocobalamin), ascorbic acid (vitamin C and derivatives of it), retinoids (such as vitamin A, retinal, and retinoic acid), vitamin D (such as vitamins D2 and D3), vitamin E and derivatives of it, carotenoids (such as carotene, lycopene, and xanthophyll), enzymes, coenzymes, and γ-oryzanol. Sphingolipids are especially preferred. Preferred sphingolipids are ceramides in which sphingosine is bonded to a fatty acid and sphingoglycolipids in which a ceramide is bonded to a sugar. The ceramides may be a natural ceramide or a synthetic ceramide and can be exemplified by Types 1 to 7 ceramides. Types 2, 5, and 7 ceramides are particularly preferred. Preferred examples of the sphingoglycolipid include cerebroside, galactosyl ceramide, and glucosyl ceramide. As the water-absorbing polymer compound and the pH controlling agent, any known substance may be used.

The low-adhesive resin 12 is preferably applied on one face alone of the mesh 11, the face being to be in contact with a wound. In other words, in the mesh 11 having a top face and a bottom face, one face alone is preferably coated with the low-adhesive resin 12. In the case that both faces of the mesh 11 are coated with the low-adhesive resin 12, the wound dressing 1 may be attached to a finger when the wound dressing 1 is gripped or the adhesive faces are attached to each other, and this complicates the attaching or changing operations on a wound area.

As described above, by designing the opening area, the number, and the perforated rate of the through-holes 111 of the mesh 11 within the particular numerical ranges, the wound dressing 1 is prevented from adhering to granulation tissues that invade the through-holes 111, can finely heal a wound surface (increase cosmetic results), and thoroughly ensure the performance of treating exudate through the through-holes 111. Therefore, the wound dressing 1 can promote fine healing of a wound area without damage, pain, and bleeding of the wound area when the wound dressing is released, while preventing the wound area and the periphery of the wound area from macerating due to exudate.

By designing the number of filaments of the multifilament constituting a knitted fabric or a woven fabric of the mesh 11 and the opening area of the through-holes 111 of the mesh 11 within the particular numerical ranges, the wound dressing 1 can be produced by a simple production method described next without causing clogging of the through-holes 111.

2. Method for Producing Wound Dressing

A method for producing the wound dressing of the present invention includes a process of applying the low-adhesive resin 12 onto the mesh 11 by transfer coating. More specifically, the production method includes a first process of applying a predetermined amount of a coating solution containing a low-adhesive resin onto a releasing base material for transfer, a second process of laminating the mesh 11 onto the base material for transfer, thereby allowing the mesh 11 to absorb the coating solution, and a third process of curing the low-adhesive resin. The method may further includes, after the third process, a fourth process of releasing the base material for transfer from the mesh 11 and a fifth process of covering a surface of the cured low-adhesive resin 12 with a release sheet. Each process will be described step by step with reference to FIG. 2.

[First Process]

First, onto a base material 4 for transfer, a predetermined amount of a coating solution 121 containing a low-adhesive resin is applied (see FIG. 2(A)). As the base material 4 for transfer, a release paper or a release film treated with a silicone release agent or a fluorine release agent or a film made of, for example, polycarbonate, polyvinyl alcohol, cellophane, and urethane may be used.

[Second Process]

Next, the base material 4 for transfer coated with the coating solution 121 is laminated with a mesh 11. By the lamination, the mesh 11 as a knitted fabric or a woven fabric formed of a multifilament absorbs the coating solution 121 (see FIG. 2(B)). At the time, by designing the number of filaments in the multifilament constituting the mesh 11 within the numerical range, the absorption amount of the coating solution 121 by the mesh 11 can be designed to a suitable amount. In other words, the coating solution 121 is absorbed by the multifilament constituting the mesh 11 and one face of the mesh 11 can be coated without closing through-holes 111.

[Third Process]

After the coating solution 121 is absorbed by the mesh 11, the mesh 11 laminated with the base material 4 for transfer is heated, thereby curing the low-adhesive resin.

[Fourth Process]

After the low-adhesive resin is cured, the base material 4 for transfer is released from the mesh 11, thereby affording a wound dressing 1 in which the mesh 11 is coated with the low-adhesive resin 12 (see FIG. 2(C)). Even when the coating solution 121 remains on the base material 4 for transfer in the second process, the coating solution 121 is cured at positions on the base material 4 for transfer corresponding to the through-holes 111 and is removed together with the base material 4 for transfer (not show in drawings). Therefore, in the obtained wound dressing 1, the low-adhesive resin 12 is unlikely to cause clogging of the through-holes 111 and almost all the through-holes 111 are kept open.

[Fifth Process]

After the low-adhesive resin is cured and the base material 4 for transfer is released from the mesh 11, the surface of the cured low-adhesive resin 12 is covered with a release sheet 5 for protection (see FIG. 2(D)).

The absorption amount of the coating solution 121 by the mesh 11 in the second process can be controlled by the number of filaments in the multifilament constituting the mesh 11. When the number of filaments is too large, the absorption amount of the coating solution 121 by the mesh 11 becomes excessively large. Thus, the coating solution 121 is absorbed by the mesh 11 into the inside and does not remain on the surface, thereby not coating the mesh 11 with the low-adhesive resin 12. When the surface of the mesh 11 is not coated with the low-adhesive resin 12, the wound dressing 1 readily adheres to a wound surface.

In contrast, when the number of filaments is too small, the absorption amount of the coating solution 121 by the mesh 11 becomes excessively small. Thus, a large amount of the coating solution 121 remains at positions on the base material 4 for transfer corresponding to the through-holes 111. When a large amount of the remaining coating solution 121 is cured in the third process, the through-holes 111 are closed. The clogging of the through-holes 111 by the low-adhesive resin 12 reduces the permeation properties of exudate through the through-holes 111.

In addition, when the mesh 11 has a too small opening area of the through-hole 111, the coating solution 121 remaining on the base material 4 for transfer readily causes the clogging of the through-holes 111. In the wound dressing 1, by designing the opening area of the through-hole 111 within the numerical range, the clogging is suppressed.

In the production method of the present invention, the number of filaments in the multifilament is designed within the particular numerical range so that the absorption amount of the coating solution 121 by the mesh 11 is a suitable amount. On this account, in the production method of the present invention, even when the amount of the coating solution 121 to be applied to the base material 4 for transfer is not strictly controlled in the first process, the surface of the mesh 11 can be coated with the low-adhesive resin 12 without closing the through-holes 111 in the third process and the fourth process. The opening area of the through-hole 111 of the mesh 11 is also designed so that the through-holes 111 do not cause clogging in the third process and the fourth process even when the amount of the coating solution 121 is not strictly controlled in the first process. Therefore, the production method of the present invention can produce a wound dressing 1 that has high permeation properties with respect to exudate and is unlikely to adhere to a wound area.

In the production method of the present invention, the low-adhesive resin 12 is applied by wet lamination. This enables the coating of one face alone of the mesh 11 with the low-adhesive resin 12 unlike dipping (immersion coating). The production method of the present invention does not cause strikethrough of the coating solution 121 unlike direct coating, and hence one face alone of the mesh 11 can be easily coated with the adhesive resin 12.

EXAMPLES

The present invention will be described in further detail based on the following examples, but the present invention is not limited to them. The properties of the wound dressing of the present invention were determined by the methods below.

[Average Opening Area of Through-Holes of Perforated Material (Unit: mm$^2$)]

The flat surface of a perforated material is observed under a microscope from the perpendicular direction (from the direction orthogonal to the flat surface of a perforated material), and the areas of five through-holes are determined and the average is calculated.

[Average Number of Through-Holes of Perforated Material (Unit: cm$^{-2}$)]

The flat surface of a perforated material is observed under a microscope from the perpendicular direction, and the number of holes present in a predetermined area is counted. The obtained number is converted into the number per cm$^2$.

[Perforated Rate of Perforated Material (Unit: %)]

The flat surface of a perforated material is observed under a microscope from the perpendicular direction, and the number of holes present in a predetermined area is counted. From the obtained number, the perforated rate is calculated based on the average opening area calculated above.

[Thickness of Perforated Material (Unit: mm)]

In accordance with JIS L 1096 "Testing methods for woven and knitted fabrics", the thickness of a perforated material before coated with a low-adhesive resin is determined.

[Diameter of Filament Constituting Multifilament (Unit: μm)]

From a multifilament, filaments constituting the multifilament are taken out and observed under a microscope. The diameters of five filaments are determined, and the average is calculated.

Example 1

A wound dressing was produced in accordance with the production method described above. Specifically, the wound dressing was produced as follows.

A two-pack addition reaction-type silicone resin (manufactured by Dow Coming, trade name "DOW CORNING 7-9800") mainly containing a vinyl group-substituted polydimethylsiloxane, an organo hydrogen polysiloxane, and a platinum catalyst was mixed and the obtained mixed solution was applied onto a fluorosilicone treated base material for transfer at a predetermined thickness. Next, onto the coated silicone resin, a perforated material made of a knitted fabric formed of a polyester multifilament was applied, and the silicone resin coating face and the perforated material were laminated. The perforated material had an average opening area of through-holes of 0.22 mm$^2$, an average through hole number of 155 cm$^{-2}$, a perforated rate of 35%, and a thickness of 330 μm. The number of filaments in the multifilament constituting the knitted fabric was 36 and the each filament had a diameter of 12 μm. Then, the whole was heated at 110° C. for 2 minutes, thereby curing the silicone resin. The base material for transfer was released, and the cured silicone resin surface was covered with a silicone release sheet, thereby affording a wound dressing.

Example 2

A wound dressing was obtained in the same manner as in Example 1 except that the average opening area of through-holes, the average through-hole number, the perforated rate, the thickness of a perforated material, and the number of filaments in the multifilament were changed as shown in "Table 1".

Example 3

A wound dressing was obtained in the same manner as in Example 1 except that the average opening area of through-holes, the average through-hole number, the perforated rate, the thickness, the number of filaments in the multifilament, and the diameter of the filament were changed as shown in "Table 1".

Comparative Example 1

A wound dressing was obtained using a perforated material in which the average opening area of through-holes and the average through-hole number were different from those of the present invention. The knitted fabric constituting the perforated material used was formed of a nylon multifilament.

Comparative Example 2

A wound dressing was obtained using a perforated material in which the average through-hole number and the number of filaments in the multifilament were different from those of the present invention.

Comparative Example 3

A wound dressing was obtained using a perforated material in which the average opening area of through-holes, the average through-hole number, the perforated rate, and the thickness were different form those of the present invention. The perforated material used was a polyurethane perforated film.

The wound dressings obtained in Examples and Comparative Examples were evaluated on the below items.

[Clogging of Through-Hole]

Evaluation of whether or not the through-holes of a perforated material were closed by a coating silicone resin was carried out.

[Cosmetic Results of Granulation on Wound Surface]

A full thickness skin defect having a diameter of 3 cm was prepared on the left abdomen of a 6-week-old male SD rat. On the prepared wound part, a sterilized wound dressing was applied and an elastic bandage was wound on the wound dressing, thereby fixing the wound dressing. After 9 days of the preparation of the wound, the wound dressing was released from the wound part. The wound surface was observed and the cosmetic results (the presence or absence of unevenness) was evaluated.

The evaluation results are shown in "Table 1" and FIG. 3. FIGS. 3(A) to 3(D) are photographs of the wound surfaces after treatment with the wound dressings of Example 1, Example 2, Comparative Example 1, and Comparative Example 3.

TABLE 1

| Properties of perforated material | Example 1 | Example 2 | Example 3 | Comparative Example 1 | Comparative Example 2 | Comparative Example 3 |
|---|---|---|---|---|---|---|
| Material | Polyester knitted fabric | Polyester knitted fabric | Polyester knitted fabric | Nylon knitted fabric | Polyester knitted fabric | Polyurethane perforated film |
| Average opening area of through-holes (mm$^2$) | 0.22 | 0.24 | 0.15 | 1.3 | 0.15 | 1.3 |
| Average through-hole number (cm$^{-2}$) | 155 | 160 | 180 | 30 | 225 | 10 |
| Number of filaments constituting multifilament | 36 | 24 | 75 | 36 | 12 | — |
| Diameter of filament constituting multifilament (μm) | 12 | 12 | 6 | 12 | 15 | — |
| Thickness of perforated material (μm) | 330 | 260 | 330 | 300 | 250 | 25 |
| Perforated rate (%) | 35 | 75 | 37 | 35 | 48 | 21 |
| Clogging of through-hole o: with clogging x: without clogging | o | o | o | o | x | o |
| Cosmetic results of wound surface o: healed into flat face x: healed into uneven face | o | o | o | x | Not performed | x |

With each wound dressing of Comparative Examples 1 and 3, an uneven face was generated on the wound surface corresponding to the shape of the perforated material and had inferior cosmetic results to the wound dressings of Examples 1 and 2. In the wound dressing of Comparative Example 2, some through-holes of the perforated material were closed by the silicone resin, resulting in clogging. It did not satisfy the basic function as a wound dressing.

In contrast, in each wound dressing obtained in Examples, the perforated material did not cause clogging, the wound dressing did not adhere to the wound, and the wound surface was healed into a flat face without unevenness.

INDUSTRIAL APPLICABILITY

The wound dressing of the present invention can promote fine healing of a wound area without damage, pain, and bleeding of the wound area when the wound dressing is released, while preventing the wound area and the periphery of the wound area from macerating due to exudate. Therefore, the wound dressing of the present invention can be suitably used to protect and treat a wound area such as a skin injury area due to burns, pressure ulcers, and other injuries and a skin grafted area.

The invention claimed is:

1. A wound dressing comprising:
   a first layer of perforated material including through-holes having a first and second face; and
   a second layer of low-adhesive resin coating said first face of the perforated material without closing the through-holes,
   wherein the perforated material is a knitted fabric or a woven fabric formed of a multifilament, and
   the perforated material has an average opening area of the through-holes of 0.02 to 1.2 mm$^2$ and an average number of through-holes of 40 to 220 holes/cm$^2$,
   wherein the perforated material has a perforated rate of 25 to 90%,
   wherein the perforated rate is calculated from an average opening area,
   wherein none of the perforated material is encapsulated by the low-adhesive resin,
   wherein the multifilament includes 15 to 100 filaments,
   wherein the multifilament is selected from the group consisting of polyester fiber, acrylic fiber, polyamide fiber, polyurethane fiber, cellulose fiber, polyolefin fiber, polyvinyl chloride fiber, polyvinylidene chloride fiber, glass fiber, and carbon fiber,
   wherein the low-adhesive resin is applied only on said first face of the perforated material,
   wherein the low-adhesive resin is only present in said second layer of the wound dressing; and
   wherein the low-adhesive resin is applied on a face that is capable of being in contact with a wound.

2. The wound dressing according to claim 1, wherein the low-adhesive resin is a silicone resin.

3. The wound dressing according to claim 1, wherein the multifilament has a diameter of 1 to 100 μm.

4. The wound dressing according to claim 1, wherein the perforated material has a thickness 50 to 1000 μm.

5. The wound dressing according to claim 1, wherein the low-adhesive resin is selected from the group consisting of silicone, acrylic resin, methacryl resin, polyvinyl chloride resin, polyvinylidene chloride resin, fluorine resin, olefinic resin, polyester resin, styrene resin, urethane resin, polyamide resin, and combinations thereof.

6. A wound dressing comprising:
   a first layer of perforated material including through-holes having a first and second face; and
   a second layer of silicone resin coating said first face of the perforated material without closing the through-holes,
   wherein the perforated material is a knitted fabric or a woven fabric formed of a multifilament,
   wherein none of the perforated material is encapsulated by the silicone resin,
   wherein the perforated material has an average opening area of the through-holes of 0.02 to 1.2 mm$^2$ and an average number of through-holes of 40 to 220 holes/cm$^2$,
   wherein the silicone resin is applied only on said first face of the perforated material, wherein the silicone resin is applied on a face that is capable of being in contact with a wound, wherein the silicone resin is only present in said second layer of the wound dressing, and wherein the wound dressing is built in layers.

7. The wound dressing according to claim 6, wherein the multifilament includes 15 to 100 filaments, wherein the silicone resin coats only said first face of the perforated material without closing the through-holes, wherein the multifilament has a diameter of 1 to 100 μm, wherein the multifilament is selected from the group consisting of polyester fiber, acrylic fiber, polyamide fiber, polyurethane fiber, cellulose fiber, polyolefin fiber, polyvinyl chloride fiber, polyvinylidene chloride fiber, glass fiber, and carbon fiber, wherein the perforated material has a thickness 50 to 1000 μm, and wherein the perforated material has a perforated rate of 25 to 90%, and wherein the perforated rate is calculated from an average opening area and average number of through-holes.

8. A wound dressing comprising:

a first layer of perforated material including through-holes having a first and second face; and a second layer of low-adhesive resin coating said first face of the perforated material without closing the through-holes, wherein the perforated material is a knitted fabric or a woven fabric formed of a multifilament, and the perforated material has an average opening area of the through-holes of 0.02 to 1.2 mm² and an average number of through-holes of 40 to 220 holes/cm², wherein the multifilament includes 15 to 100 filaments, wherein the low-adhesive resin coats only said first face of the perforated material without closing the through-holes, wherein the multifilament has a diameter of 1 to 100 μm, wherein the multifilament is selected from the group consisting of polyester fiber, acrylic fiber, polyamide fiber, polyurethane fiber, cellulose fiber, polyolefin fiber, polyvinyl chloride fiber, polyvinylidene chloride fiber, glass fiber, and carbon fiber, wherein the perforated material has a perforated rate of 25 to 90%, wherein the perforated rate is calculated from an average opening area and average number of through-holes, wherein the low-adhesive resin is selected from the group consisting of silicone, acrylic resin, methacryl resin, polyvinyl chloride resin, polyvinylidene chloride resin, fluorine resin, olefinic resin, polyester resin, styrene resin, urethane resin, polyamide resin, and combinations thereof, wherein none of the perforated material is encapsulated by the low-adhesive resin, wherein the low-adhesive resin is applied only on said first face of the perforated material, wherein the low-adhesive resin is only present in said second layer of the wound dressing, wherein the low-adhesive resin is applied on a face that is capable of being in contact with a wound, and wherein the wound dressing is built in layers.

\* \* \* \* \*